(12) United States Patent
Natarajan et al.

(10) Patent No.: US 11,458,261 B2
(45) Date of Patent: Oct. 4, 2022

(54) CURCUMIN STIMULATOR

(71) Applicants: Vijaya Natarajan, Concord, NH (US); Joanne Michelle Martin, Concord, NH (US)

(72) Inventors: Vijaya Natarajan, Concord, NH (US); Joanne Michelle Martin, Concord, NH (US)

( * ) Notice: Subject to any disclaimer, the term of this patent is extended or adjusted under 35 U.S.C. 154(b) by 0 days.

(21) Appl. No.: 17/082,134

(22) Filed: Oct. 28, 2020

(65) Prior Publication Data

US 2022/0126029 A1  Apr. 28, 2022

(51) Int. Cl.
*A61M 11/04* (2006.01)
*A61M 15/00* (2006.01)

(52) U.S. Cl.
CPC .......... *A61M 11/041* (2013.01); *A61M 11/04* (2013.01); *A61M 11/048* (2014.02); *A61M 15/0003* (2014.02); *A61M 2202/04* (2013.01); *A61M 2202/06* (2013.01); *A61M 2205/59* (2013.01)

(58) Field of Classification Search
CPC ... A61L 2/04; A61L 9/02–037; A61M 11/041; A61M 11/048; A01M 1/2061; B05B 1/24; B05B 9/002; B05C 5/001; B05C 11/1042; B05C 17/00523; B05C 3/005; B67D 7/80; B67D 7/82; A47J 31/20; A47J 31/14; A47J 31/34; A47J 31/4407; A47J 43/046; A47J 43/1081; A47J 27/2105; A47J 31/04; B65D 85/816
USPC ....... 239/34–60, 135, 136, 386, 53–60, 145; 261/28; 422/125, 5; 222/146.2; 392/394–406, 386, 20; 268/DIG. 88, 268/DIG. 89; 99/297, 295, 317, 322, 99/323, 323.3
See application file for complete search history.

(56) References Cited

U.S. PATENT DOCUMENTS

| | | | | |
|---|---|---|---|---|
| 325,980 | A * | 9/1885 | Shaw | A47J 27/04 126/369 |
| 447,678 | A * | 3/1891 | Gibson | A47J 27/04 126/369 |
| 99,571,811 | | 11/1896 | Valentine | |
| 99,843,705 | | 2/1907 | Seligsohn | |
| 1,202,485 | A | 10/1916 | Cohn | |
| 2,061,148 | A * | 11/1936 | Fischer | A61M 11/041 392/403 |

(Continued)

*Primary Examiner* — Justine R Yu
*Assistant Examiner* — Alexander Morales
(74) *Attorney, Agent, or Firm* — Joanne M. Martin

(57) ABSTRACT

A curcumin entrained vapor generator providing the release of an essence, or compound or substances, from a solid or powder or liquid into a vapor exiting the generator, comprising a container having an interior volume and a region disposed to contain a liquid which emits or forms a vapor, and an openable closed end distal from said contained liquid. An interior support formed to support material (e.g. curcumin or other) thereon and is included and has a plurality of openings, and is dimensioned less than said container interior dimension across said container liquid to form a large vapor passage allowing the essence of the included material to be gently released into the vapor of the liquid and released into the external environment via the container openings. Other embodiments include esthetically shaped support structures, e.g. a leaf, a plant twig-like arms, etc. and/or graphic overlays, etchings, engravings, etc.

13 Claims, 1 Drawing Sheet

(56) References Cited

U.S. PATENT DOCUMENTS

| | | | | |
|---|---|---|---|---|
| 2,522,718 A * | 9/1950 | Huck | A61M 11/041 | 392/403 |
| 2,526,027 A * | 10/1950 | Huck | A61M 11/041 | 422/125 |
| 2,662,965 A * | 12/1953 | Becker | A47J 47/14 | 219/415 |
| 2,822,459 A * | 2/1958 | Kamin | A61M 15/00 | 392/403 |
| 3,143,059 A * | 8/1964 | Sofio | A47J 27/04 | 99/418 |
| 3,398,827 A * | 8/1968 | Laskin | B65D 1/36 | 206/541 |
| 3,583,307 A * | 6/1971 | Lee, Sr. | A47J 27/08 | 219/431 |
| 3,724,359 A * | 4/1973 | Masters | A47J 31/20 | 99/281 |
| 3,802,330 A * | 4/1974 | Graziani | A47J 37/00 | 99/421 H |
| 4,595,564 A | 6/1986 | Spector | | |
| 4,953,452 A * | 9/1990 | Tarlow | A47J 27/212 | 99/344 |
| D336,727 S * | 6/1993 | Skerker | A23L 5/13 | D7/409 |
| 5,320,028 A * | 6/1994 | Grunberg | A47J 36/18 | 126/369 |
| 5,349,898 A * | 9/1994 | Po Wo Cheung | A47J 36/20 | 126/369 |
| 5,520,099 A * | 5/1996 | Chung | A23L 5/15 | 219/731 |
| 5,758,569 A * | 6/1998 | Barbour | A47J 37/1204 | 99/415 |
| 5,967,020 A * | 10/1999 | Soyama | A21B 3/04 | 99/417 |
| 6,371,453 B1 | 4/2002 | Hunter | | |
| 6,711,992 B1 * | 3/2004 | McLemore | A47J 27/04 | 99/339 |
| 6,767,521 B1 * | 7/2004 | Vogt | A61L 9/012 | 206/0.5 |
| 6,875,959 B1 * | 4/2005 | Ciejek | A47J 27/04 | 126/20.2 |
| 9,271,594 B1 * | 3/2016 | Roth | A23L 5/13 | |
| 10,548,432 B1 * | 2/2020 | Pugh | A21B 3/135 | |
| 2004/0200359 A1 * | 10/2004 | Snider | A47J 37/0704 | 99/446 |
| 2006/0260598 A1 * | 11/2006 | Bjork | A23B 4/044 | 126/9 A |
| 2009/0049990 A1 * | 2/2009 | Schutte | A47J 36/22 | 99/339 |
| 2009/0078125 A1 * | 3/2009 | Pawlick | B65D 21/0209 | 99/448 |
| 2010/0064903 A1 * | 3/2010 | Spence | A47J 36/18 | 99/415 |
| 2010/0255168 A1 * | 10/2010 | Roth | A23L 5/13 | 426/510 |
| 2012/0036771 A1 * | 2/2012 | Harshman | A01G 9/023 | 47/41.01 |
| 2015/0342172 A1 * | 12/2015 | Sharma | A01M 29/14 | 43/124 |
| 2018/0184848 A1 * | 7/2018 | De'Longhi | A47J 43/046 | |
| 2019/0160193 A1 * | 5/2019 | Mubarak | A61L 9/03 | |
| 2020/0359823 A1 * | 11/2020 | Griffin | A47J 27/04 | |

\* cited by examiner

CURCUMIN STIMULATOR

FIELD OF THE INVENTION

The present invention relates to vaporizers, in particular to vaporizers which entrain the essence of substances or compounds in a vapor carrier.

BACKGROUND

Anxiety is the reaction that humans have evolved over the term of evolution and affects the body's response to threats, and may be controlled somewhat by the ambient environment including the release of substances into that environment. Moreover, at the heart of public health is the effective use of measures and apparatus to fortify human resistance to pathogens even while there are absolutely no symptoms or only mild symptoms. For instance, steam vaporizers allow steam inhalation for invigorating the lungs and may help alleviate dry air and problems associated with a cold or the flu. Introducing a substance to the vapor may be used for palliative or therapeutic purposes. However, the effective addition of essences of substances to a vapor depends on the substance, the vapor, and the use of an apparatus or process for one combination that may be counterproductive in another setting.

An exemplary combination of the introduction of the essence of curcumin (or similar) in a flow of water vapor enriched air may provide a pleasing effect and sensation to open up, or 'stimulating' the inhaling and exhaling in the nearby environment. However, it is believed substances like curcumin require more gentle and controlled exposure to vapor, and that settings to force maximum essence extraction by placing the contained substance so that it substantially occludes a passage between a source of boiling water and the open external environment will improperly interact with the curcumin and interfere with the release of the desired quality of curcumin (or other substance) essence, or also cause the release of other, unwanted components into the flow of steam or vapor.

SUMMARY

The curcumin stimulator according to one embodiment includes a vapor generator providing the release of an essence, or compound or substances, from a solid or liquid into a vapor exiting the generator, comprising a container having an interior volume and a region disposed to contain a liquid which emits or forms a vapor, and an openable and/or perforated closed end distal from said contained liquid. Typically, the closed end comprises or includes a cover disposed to engage a container open end, and has a plurality of openings therein permitting communication and release of vapor between the interior volume and region exterior to said container. An interior support formed to support material (e.g. curcumin or other) thereon and is included and disposed apart from (typically below) the container end having the plurality of openings thereon, and is dimensioned less than the container interior dimension across the container liquid to form a large vapor passage or region between the liquid and the interior support peripheral dimension, allowing the essence of the included material to be gently released into the vapor of the liquid and released into the external environment via the container openings. The region of the container holding the liquid of the exemplary embodiment may receive external or internal heat energy to warm the liquid (typically water) to controllably form vapor or steam.

Other embodiments include substantially planar substance support structures having openings of different sizes, and small cup-shaped substance holders that may additionally contain powder or liquid substances whose essence will be released into the vapor. Further embodiments provide esthetically shaped support structures, e.g. a leaf, a plant twig-like arms, etc. and/or visual designs, e.g. an 'eye' formed to include the support openings or shape and/or graphic overlays, etchings, engravings, etc.

BRIEF DESCRIPTION OF THE DRAWING

These and further features of the present invention will be further understood by reading the following Detailed Description, taken together with the Drawings, wherein.

DETAILED DESCRIPTION

Figure 1:
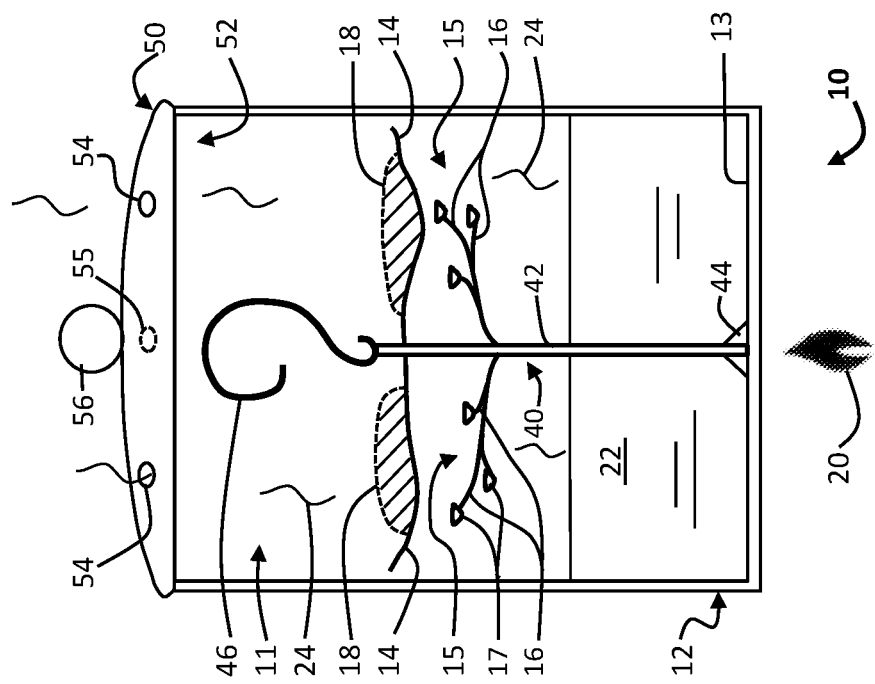
FIG. 1 is an elevation cross section of one embodiment of the present invention.

An embodiment 10 of the present invention shown in FIG. 1 comprises a container 12, a perforated substance support 14 for retaining a substance 18 (e.g. curcumin), and a container lid 50. The container 12 includes water 22 that is heated by and external heat source 20 to said container when upright as shown, on a container region disposed to contain the liquid water (or internal heat source not shown) sufficient to generate water vapor 24 within the interior 11 of the container 12, and preferably heat sufficient to provide a warm or gentle boiling of the water sufficient to produce vapor around the desired medium 18 to transfer the essence of the substance 18 outside the container 12. The preferable amount of water 22 level is approximately up to mid-way between the container 12 interior bottom 13 and the perforated support 14 vertical position, but other amounts of water (or other liquid) that do not splash (when heated) on, or contact the perforated support 14 are acceptable.

An alternate or additional substance support 15 typically comprises individual arms 16 having small cup-like holders 17 to each retain small amounts of a solid, powder or liquid substance the same as or different from the substance retained on substance support 14. The individual arms 16 may join at a common point or may connect at different places, as shown.

An interior support 40 is attached to the perforated supports 14 and/or additional supports 15 and comprises vertical support 42 and typically a conical or a tripod-like base 44 to provide stable support within container interior 11, or similar broadened shape, to rest on the interior bottom 13 of the container 12. Other supports embodiments, the support 42 may comprise a rod (not shown) releasably received in a hole (not shown) in the base 42 of any shape fastened to the interior bottom 13 of the container 12 from which the vertical support may be released for loading of the substances 18.

A lifting member 46 is attached to the perforated support generally away and in a direction opposite from the vertical support 42 and a height greater than the support(s) that contain aromatic material 18, and may comprise an "S" shape or other desired feature useful to remove the perforated support 14 from the container 12 interior, and is preferably a thermal insulator and/or heat resistant material, e.g. certain plastics or Bakelite™, to permit handling without injury and minimum discomfort when the embodiment is in operation.

Figure 2:
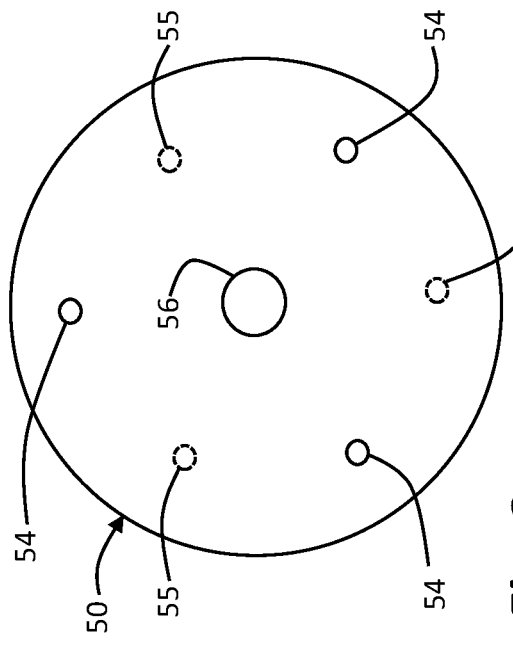
FIG. 2 is a plan view of a lid according to the embodiment of FIG. 1.

The lid 50 of the embodiment of FIG. 1 and shown in the plan view of FIG. 2, engages the interior dimension open end 52 to be retained thereon. The lid 50 includes (typically 3 each) openings 54 to permit the substance-entrained vapor 24 to be slowed in its emergence from the container 12 via the lid 50 openings 54, to gain the desired essence from the material 18. Typically, the openings 54 are fewer in number (preferably 3) than support 14 perforations, and have a total opening area less than the container interior 11 horizontal dimensions, or less than the perforated support 14 openings 26, 30 to retard vapor emission from the stimulator. Additional lid openings 55 may be added as desired and in accordance with the operation of the present invention. The lid 50 further include a knob 56 or equivalent or suitable shape attached to the lid 50 to permit lifting from the container 12 and preferably comprising a thermal insulator and/or heat resistant material described above. The lid is typically disposed on the open end of the container 12 and may include a downward extending (into the container interior 11) ridge (not shown) or other structure to sufficiently engage the container 12 opening and seal the open end so that vapor is emitted (via holes 54, 55, and/or other openings) according to the present invention.

Figure 3:
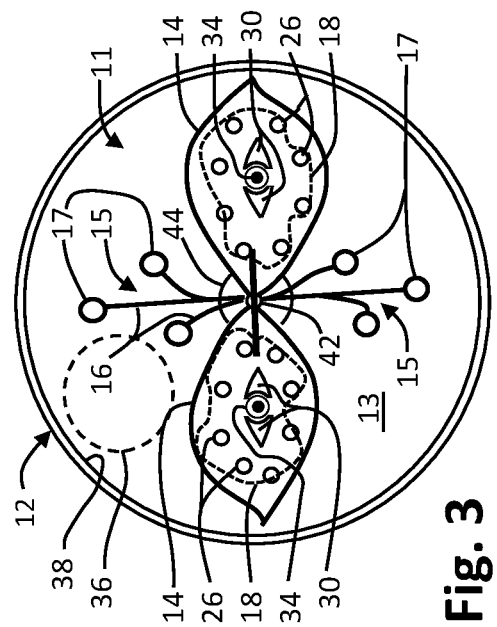
FIG. 3 is a plan view of the container and holder according to the embodiment of FIG. 1.

As shown in the plan view of FIG. 3 looking into the open end of the container 12 interior 11 (the water 22 and the vapor 24 being omitted for clarity), the perforated support 14 receives aromatic material 18 preferably includes a plurality (e.g. 8) small openings 26 that in one embodiment have the same area, sufficient to allow the water vapor 24 to pass through to the aromatic material 18. Additionally, there are relatively larger openings 30 that may be shaped according to a desired ornamental feature, e.g. an 'eye' to suggest elliptical eye 'whites' as the openings 30 and the 'pupil' 34 is solid, and may include a desired ornamental design thereon by overlay, etching, etc. The aromatic 20 material 18 typically comprises small pieces of curcumin, or other aromatic, organic, or therapeutic medicinal material sufficiently large relative to bridge the openings 26, 30, etc., to be retained on the support 14 and receive and interact with the water vapor 24 and release its corresponding substance essence into the vapor (24). The supports 14 are/is shaped and dimensioned to have a shape and horizontal span less than the interior dimension of the container 12, and as shown in FIG. 3, supports 14 and 15 each has a horizontal dimension comprising a minor portion of the container 12 corresponding (to its horizontal direction and vertical position) interior horizontal dimensions and an area comprising a minor portion of the container 12 corresponding area and each supports. e.g. 14 and 15, may comprise a single surface as shown, and provide unobstructed water vapor passage(s) 36 between the perforated support 14 and/or holder 17 and the interior wall 38 of the container, the unobstructed vapor passage(s) comprising a major portion (more than half) of the area of the container inner area at a distance above the container 12 bottom which supports, e.g. 14 and 15, are retained. The perforated support 14 may also comprise or include an arm attached to and extending away from the vertical support 42, and/or an ornamental shape, e.g. butterfly wings, leaves, etc. and the support 15 may resemble nature-related shapes such as a twig with end 'fruit'. In addition to curcumin, the material 18 retained on the support may also comprise cloves, *eucalyptus*, clove, and spices.

The alternate or additional support 15 and arms with holders 17 are shown attached to the vertical support 42, which is in turn, received by the base 44 for support within the container 12. In the embodiments shown, the supports 14 are shown on opposite sides of the vertical support 42, as are the supports 15 shown on opposite sides of the vertical support. FIG. 1 shows the supports 15 generally aligned below and spaced from the supports 14, while FIG. 3 shows the supports 15 orthogonally aligned relative to the supports 14, as may be desired. Other numbers and dispositions of supports 14 and/or 15 that position substance(s) above the water (22) and within the vapor (24) are within the scope of the present invention.

As therapeutic substances are found to be medically effective when released according to the present invention, the apparatus and methods according to the present invention are applicable thereto. These and further embodiments, modifications and substitutions made by one of ordinary skill ae within the scope of the present invention.

What is claimed is:
1. A vapor generator, comprising:
a container having an interior volume, a bottom, a region disposed to contain a liquid, and an interior area with a dimension across said contained liquid at a distance above said bottom, and an open end distal from said contained liquid;
an interior support for holding a substance disposed within said container apart from said container open end within said container at said distance above said bottom,
said interior support having a plurality of openings thereon,
and having an interior support area and horizontal dimensions less than a corresponding said container interior horizontal dimension and container interior area at said distance above said bottom,
and at least one of said interior support horizontal dimensions comprising a minority portion of said container interior horizontal dimension at said distance above said bottom,
and said interior support area comprising a minority portion of said container interior area at said distance above said bottom to form a vapor passage between said region disposed to contain a liquid and said interior support horizontal dimensions at said distance above said bottom,
and at said distance above said bottom, said vapor passage between said interior support area and said container interior area comprising a majority of said container interior area, providing gentle stimulation and release of an essence, or compound or substances from said substance held by said interior support into vapor provided by said contained liquid; and
a cover disposed to engage said container open end having a plurality of openings therein permitting communication between said interior volume and region exterior to said container permitting release of a vapor having of an essence, or compound or substances from said substance, wherein
the interior support is housed within a cylindrical interior surface of the container, and wherein
a gap, forming a portion of the vapor passage, is created and positioned between the cylindrical interior surface and a vertical exterior surface of the interior support such that the portion of the vapor passage is an unobstructed water vapor path that does not flow through the openings of the support.

2. The vapor generator of claim 1, wherein the interior support is disposed below said cover plurality of openings.

3. The vapor generator of claim 1, wherein said interior support includes a substantially planar member having the plurality of openings therein.

4. The vapor generator of claim 3, wherein the plurality of openings of the substantially planar member include eight apertures and each of said apertures having same aperture area and at least one larger aperture.

5. The vapor generator of claim 1, wherein said interior support comprises a vertical member extending from said bottom, at least one substance holder attached to and extending away from said vertical member, and said at least one substance holder is an arm connected to said vertical member and having an unconnected end, or includes an arm having an end away from said vertical member to which the substance holder is retained.

6. The vapor generator of claim 1, wherein said interior support includes a bottom support disposed to rest on the container bottom.

7. The vapor generator of claim 6, wherein said interior support further includes an S-shaped lifting member opposite from said bottom support, and comprising heat insulator material.

8. The vapor generator of claim 1, wherein said interior support includes substance holders comprising ornamental holders.

9. The vapor generator of claim 1, wherein said plurality of openings of said cover, together form an open area less than said container interior area.

10. The vapor generator of claim 9, wherein said cover plurality of openings comprises three openings.

11. The vapor generator of claim 1, wherein said cover further including an upward extending lifting member comprising thermal insulating material.

12. The vapor generator of claim 1, further including a heat source disposed to apply heat energy to said bottom of the container.

13. A vapor generator, comprising:
a container having an interior volume, a bottom, a region disposed to contain a liquid including said bottom, and an interior area with a horizontal dimension across said contained liquid at a distance vertically above said bottom, and an open end distal from said bottom;
an interior support for holding a substance disposed within said container apart from said container open end within said container at said distance above and apart from said bottom, wherein
said interior support comprises a single surface and having an opening therein and a periphery,
and an area and horizontal dimensions less than a corresponding said container interior horizontal dimension and interior area at said distance above said bottom,
and at least one of said interior support horizontal dimensions comprising less than half of said container interior horizontal dimension at said distance above said bottom,
and said interior support area comprising less than half of said container interior area at said distance above said bottom to form a vapor passage between said region disposed to contain a liquid and said interior support horizontal dimensions at said distance above said bottom,
and at said distance above said bottom, said vapor passage between said interior support area and said container interior area comprising more than half of said container interior area, providing gentle vapor stimulation of said substance held by said interior support from vapor provided by said contained liquid; and
a cover disposed to engage said container open end having a plurality of openings therein permitting communication between said interior volume and region exterior to said container permitting release of vapor having of an essence, or compound or substances released from said substance, wherein
the interior support is housed within a cylindrical interior surface of the container, and wherein
a gap, forming a portion of the vapor passage, is created and positioned between the cylindrical interior surface and said periphery of said single surface of the interior support such that the portion of the vapor passage is an unobstructed water vapor path that does not flow through the opening of the support.

* * * * *